United States Patent [19]
Baker

[11] Patent Number: 5,932,574
[45] Date of Patent: Aug. 3, 1999

[54] QUINAZOLINE DERIVATIVES

[75] Inventor: Andrew John Baker, Macclesfield, United Kingdom

[73] Assignee: Zeneca Limited, London, United Kingdom

[21] Appl. No.: 08/930,041

[22] PCT Filed: Apr. 23, 1996

[86] PCT No.: PCT/GB96/00958

§ 371 Date: Sep. 26, 1997

§ 102(e) Date: Sep. 26, 1997

[87] PCT Pub. No.: WO96/33977

PCT Pub. Date: Oct. 31, 1996

[30] Foreign Application Priority Data

Apr. 27, 1995 [GB] United Kingdom ............... 9508566
Apr. 27, 1995 [GB] United Kingdom ............... 9508568

[51] Int. Cl.⁶ ............... C07D 239/94; A61K 31/505
[52] U.S. Cl. ............... 514/234.5; 514/259; 544/119; 544/293
[58] Field of Search ............... 544/119, 293; 514/234.5, 259

[56] References Cited

U.S. PATENT DOCUMENTS

| | | | |
|---|---|---|---|
| 3,266,990 | 8/1966 | Lutz et al. | 514/259 |
| 4,343,940 | 8/1982 | Kreighbaum et al. | 514/259 |
| 5,373,011 | 12/1994 | Haley | 514/259 |
| 5,411,963 | 5/1995 | Dreikom et al. | 514/259 |
| 5,457,105 | 10/1995 | Barker | 514/234.5 |
| 5,571,815 | 11/1996 | Schaper et al. | 514/259 |
| 5,616,582 | 4/1997 | Barker | 514/234.5 |

FOREIGN PATENT DOCUMENTS

| | | |
|---|---|---|
| 0 326 307 | 2/1989 | European Pat. Off. . |
| 0 326 330 A2 | 8/1989 | European Pat. Off. . |
| 0 520 722 A1 | 12/1992 | European Pat. Off. . |
| 566 226 | 10/1993 | European Pat. Off. . |
| 0 602 851 A1 | 6/1994 | European Pat. Off. . |
| 0 635 507 A1 | 1/1995 | European Pat. Off. . |
| 635 498 | 1/1995 | European Pat. Off. . |
| 0 682 027 A1 | 11/1995 | European Pat. Off. . |
| 0 787 722 A1 | 8/1997 | European Pat. Off. . |
| 2 033 894 | 5/1980 | United Kingdom . |
| 2 160 201 | 12/1985 | United Kingdom . |
| WO 97/13760 | 4/1977 | WIPO . |
| WO 97/13771 | 4/1977 | WIPO . |
| WO 92/14716 | 9/1992 | WIPO . |
| WO 92/20642 | 11/1992 | WIPO . |
| WO 95/06648 | 3/1995 | WIPO . |
| WO 95/15758 | 6/1995 | WIPO . |
| WO 95/15952 | 6/1995 | WIPO . |
| WO 95/19169 | 7/1995 | WIPO . |
| WO 95/19774 | 7/1995 | WIPO . |
| WO 95/19970 | 7/1995 | WIPO . |
| WO 95/21613 | 8/1995 | WIPO . |
| WO 95/23141 | 8/1995 | WIPO . |
| WO 95/24190 | 9/1995 | WIPO . |
| WO 96/07657 | 3/1996 | WIPO . |
| WO 96/09294 | 3/1996 | WIPO . |
| WO 96/15118 | 5/1996 | WIPO . |
| WO 96/16960 | 6/1996 | WIPO . |
| WO 96/29331 | 9/1996 | WIPO . |
| WO 96/30347 | 10/1996 | WIPO . |
| WO 96/31510 | 10/1996 | WIPO . |
| WO 96/33977 | 10/1996 | WIPO . |
| WO 96/33978 | 10/1996 | WIPO . |
| WO 96/33979 | 10/1996 | WIPO . |
| WO 96/33980 | 10/1996 | WIPO . |
| WO 96/33981 | 10/1996 | WIPO . |
| WO 96/34867 | 11/1996 | WIPO . |
| WO 96/35689 | 11/1996 | WIPO . |
| WO 96/39145 | 12/1996 | WIPO . |
| WO 96/40142 | 12/1996 | WIPO . |
| WO 96/40648 | 12/1996 | WIPO . |
| WO 97/02266 | 1/1997 | WIPO . |
| WO 97/03069 | 1/1997 | WIPO . |
| WO 97/18212 | 5/1997 | WIPO . |

OTHER PUBLICATIONS

Rewcastle et al., "Tyrosine Kinase Inhibitors. 5. Synthesis and Structure–Activity Relationships for 4–[(Phenylmethyl)amino]– and 4–(Phenylamino)quinazolines as Potent Adenosine 5'–Triphosphate Binding Site Inhibitors of the Tyrosine Kinase Domain of the Epidermal Growth Factor Receptor," J.Med.Chem. 1995, vol. 38, pp. 3482–3487.

Burke, Jr., "Protein–tyrosine kinase inhibitors," Drugs of the Future 1992, vol. 17(2), pp. 119–131.

Spence, "Inhibitors of Tyrosine Kinase Activity as Anticancer Therapeutics: Recent Developments," Expert Opinion in Therapeutic Patents, Jan. 1993, Patent Update, Anticancers, etc., pp. 3–9, Current Drugs Ltd ISSN 0962–2594,.

Spada et al., Small molecule inhibitors of tyrosine Kinase activity, Exp.Opin.Ther.Patents (1995), 5(8):805–817, Patent Update, Oncologic, Endocrine & Metabolic, Ashley Publications Ltd ISSN 1354–3776.

Bridges, "The current status of tyrosine kinase inhibitors: do the diarylamine inhibitors of the EGF receptor represent a new beginning?," Exp.Opin.Ther.Patents (1995), 5(12): 1245–1257, Editorial, Oncologic, Endocrine & Metabolic, 1995 Ashley Publications Ltd ISSN 1354–3776.

Traxler et al., "Recent advances in protein tyrosine kinase inhibitors," Drugs of the Future 1995, vol. 20(12, pp. 1261–1274.

(List continued on next page.)

Primary Examiner—John M. Ford
Attorney, Agent, or Firm—Cushman Darby & Cushman; Intellectual Property Group of Pillsbury; Madison & Sutro, LLP

[57] ABSTRACT

The invention concerns quinazoline derivatives of formula wherein n is 1, 2 or 3 and each $R^2$ is independently halogeno; and $R^1$ is di-[(1–4C)alkyl]amino-(2–4C)alkoxy, pryolidin-1-yl-(2–4C)alkoxy,piperidino-(2–4C)alkoxy, morpholino-(2–4C)alkoxy, piperazin-1-yl-(2–4C)alkoxy or 4-(1–4C) alkylpiperazin-1-yl-(2–4C)alkoxy; or pharmaceutically-acceptable salts thereof; processes for their preparation, pharmaceutical compositions containing them, and the use of the receptor tyrosine kinase inhibitory properties of the compounds in the treatment of proliferative disease such as cancer.

8 Claims, No Drawings

OTHER PUBLICATIONS

Iyer et al., "Studies in Potential Amoebicides: Part III–Synthesis of $_4$–Substituted Amino–8–Hydroxy) Quinazolines & $_3$–Substituted 8–Hydroxy(&8–Methoxy)–$_4$–Quinazolones," J.Sci.Industr.Res., vol. 15C, Jan. 1956, pp. 1–7.

Kobayashi, Derwent Abstract 82–87077, vol. 6, No. 244, Dec. 1982, JP 57–144266, Sep. 1982, "4–Anilinoquinazoline Derivative, its Preparation and Analgesic and Antiphlogistic Agent Containing Said Derivative as Active Component".

Sankyo and Ube, Derwent Abstract 81–28290, JP 56–20577, Feb. 1981, "4–(N–alkyl:anilino) quinazoline derivs . . . having analgesic and antiinflammatory actions".

Kyorin, Derwent Abstract 84–53835, JP 59–13765, Jan. 1984, "2–(4–Quinazolinyl)amino benzoic acid derivs . . . having analgesic and antiinflammatory activities".

Li et al., Chem.Abs., vol. 92:76445u, 1980, pp. 674–675.

Lin et al., Chem.Abs., vol. 96:122728w, 1982, p. 695.

Fry et al., "A Specific Inhibitor of the Epidermal Growth Factor Receptor Tyrosine Kinase," SCIENCE, vol. 265, Aug. 19, 1994, pp. 1093–95.

Buchdunger et al., "4,5–Dianilinophthalimide: A protein–tyrosine kinase inhibitor with selectivity for the epidermal growth factor receptor signal transduction pathway and potent in vivo antitumor activity," Proc.Natl.Acad.Sci., USA, vol. 91, pp. 2334–2338, Mar. 1994, Applied Biological Sciences.

Trinks et al., "Dianilinophthalimides: Potent and Selective, ATP–Competitive Inhibitors of the EGF–Receptor Protein Tyrosine Kinase," J.Med.Chem. 1994, Vol. 37, pp. 1015–1027.

Maguire et al., "A New Series of PDGF Receptor Tyrosine Kinase Inhibitors: 3–Substituted Quinoline Derivatives," J.Med.Chem. 1994, vol. 37, pp. 2129–2137.

Dolle et al., "5,7–Dimethoxy–3–(4–pyridinyl)quinoline Is a Potent and Selective Inhibitor of Human Vascular β–Type Platelet–Derived Growth Factor Receptor Tyrosine Kinase," J.Med.Chem. 1994, vol. 37, pp. 2627–2629.

Bridges et al., "Enantioselective Inhibition of the Epidermal Growth Factor Receptor Tyrosine Kinase by 4–(α–Phenethylamino)quinazolines," Bioorganic & Medicinal Chemistry, vol. 3, No. 12, pp. 1651–1656, 1995.

Ward et al., "Epidermal Growth Factor Receptor Tyrosine Kinase—Investigation of Catalytic Mechanism, Structure–Based Searching and Discovery of a Potent Inhibitor," Biochem.Pharmacology, vol. 48, No. 4, pp. 659–666 (1994).

Agrawal, "Studies on Potential Filaricides: Part XI", Chemical Abstracts, vol. 95, No. 1, 1981, Abstract No. 7199s, pp. 682–683; see abstract in Indian J. Chem. Sect. B, vol. 19B, No. 12, 1980, INDIA, pp. 1084,1087.

Connolly, et al., "Human Vascular Permeability Factor," J.Bio.Chem., vol. 264, No. 33, Nov. 1989, pp. 20017–20024.

Cullinan–Bove, et al., "Vascular Endothelial Growth Factor/Vascular Permeability Factor Expression in the Rat Uterus . . . ," Endocrinology, vol. 133, No. 2, 1993, pp. 829–837.

Fan et al., "Controlling the Vasculature: Angiogenesis, Anti–Angiogenesis . . . ," TiPS Review, vol. 16, Feb. 1995, pp. 57–65.

Folkman, "Angiogenesis in Cancer, Vascular, Rheumatoid and Other Disease," Nature Medicine, vol. 1, No. 1, 1995, pp. 27–30.

Jakeman et al., "Developmental Expression of Binding Sites and Messenger Ribonucleic Acid . . . ," Endocrinology, vol. 133, No. 2, 1993, pp. 848–859.

Kim et al., "Inhibition of Vascular Endothelial Growth Factor–Induced Angiogenesis Suppresses Tumour Growth in Vivo," Nature, vol. 362, Apr. 1993, pp. 841–844.

Kolch et al., "Regulation of the Expression of the VEGF/VPS and its Receptors: Role in Tumor Angiogenesis," Breast Cancer Research and Treatment, vol. 36, 1995, pp. 139–155.

Senger et al., "Vascular Permeability Factor (VPF, VEGF) in Tumor Biology, "Cancer and Metastasis Review, vol. 12, 1993, pp. 303–324.

QUINAZOLINE DERIVATIVES

This application is the national phase of international application PCT/GB95/00958, filed Apr. 23 1996 which designated the U.S.

The invention relates to quinazoline derivatives, or pharmaceutically-acceptable salts thereof, which possess anti-proliferative activity such as anti-cancer activity and are accordingly useful in methods of treatment of the human or animal body. The invention also relates to processes for the manufacture of said quinazoline derivatives, to pharmaceutical compositions containing them and to their use in the manufacture of medicaments of use in the production of an anti-proliferative effect in a warm-blooded animal such as man.

Many of the current treatment regimes for cell proliferation diseases such as psoriasis and cancer utilise compounds which inhibit DNA synthesis. Such compounds are toxic to cells generally but their toxic effect on rapidly dividing cells such as tumour cells can be beneficial. Alternative approaches to anti-proliferative agents which act by mechanisms other than the inhibition of DNA synthesis have the potential to display enhanced selectivity of action.

In recent years it has been discovered that a cell may become cancerous by virtue of the transformation of a portion of its DNA into an oncogene i.e. a gene which, on activation, leads to the formation of malignant tumour cells (Bradshaw, *Mutagenesis,* 1986, 1, 91). Several such oncogenes give rise to the production of peptides which are receptors for growth factors. The growth factor receptor complex subsequently leads to an increase in cell proliferation. It is known, for example, that several oncogenes encode tyrosine kinase enzymes and that certain growth factor receptors are also tyrosine kinase enzymes (Yarden et al., *Ann. Rev. Biochem.,* 1988, 57, 443; Larsen al. *Ann. Reports in Med. Chem.* 1989, Chpt. 13).

Receptor tyrosine kinases are important in the transmission of biochemical signals which initiate cell replication. They are large enzymes which span the cell membrane and possess an extracellular binding domain for growth factors such as epidermal growth factor (EGF) and an intracellular portion which functions as a kinase to phosphorylate tyrosine amino acids in proteins and hence to influence cell proliferation. Various classes of receptor tyrosine kinases are known (Wilks, *Advances in Cancer Research,* 1993, 60, 43–73) based on families of growth factors which bind to different receptor tyrosine kinases. The classification includes Class I receptor tyrosine kinases comprising the EGF family of receptor tyrosine kinases such as the EGF, TGFα, NEU, erbB, Xmrk, HER and let23 receptors, Class II receptor tyrosine kinases comprising the insulin family of receptor tyrosine kinases such as the insulin, IGFI and insulin-related receptor (IRR) receptors and Class III receptor tyrosine kinases comprising the platelet-derived growth factor (PDGF) family of receptor tyrosine kinases such as the PDGFα, PDGFβ and colony-stimulating factor 1 (CDF1) receptors. It is known that Class I kinases such as the EGF family of receptor tyrosine kinases are frequently present in common human cancers such as breast cancer (Sainsbury et al., *Brit J. Cancer,* 1988, 58, 458; Guerin et al., *Oncogene Res.,* 1988, 3, 21 and Klijn et al., *Breast Cancer Res. Treat.,* 1994, 29, 73), non-small cell lung cancers (NSCLCs) including adenocarcinomas (Cerny et al., *Brit. J. Cancer,* 1986, 54, 265; Reubi et al., *Int. J. Cancer,* 1990, 45, 269; and Rusch et al., *Cancer Research,* 1993, 53, 2379) and squamous cell cancer of the lung (Hendler et al., *Cancer Cells,* 1989, 7, 347), bladder cancer (Neal et al., *Lancet,* 1985, 366), oesophageal cancer (Mukaida et al., *Cancer,* 1991, 68, 142), gastrointestinal cancer such as colon, rectal or stomach cancer (Bolen et al., *Oncogene Res.,* 1987, 1, 149), cancer of the prostate (Visakorpi et al., *Histochem. J.,* 1992, 24, 481), leukaemia (Konaka et al., *Cell,* 1984, 37, 1035) and ovarian, bronchial or pancreatic cancer (European Patent Specification No. 0400586). As further human tumour tissues are tested for the EGF family of receptor tyrosine kinases it is expected that their widespread prevalance will be established in further cancers such as thyroid and uterine cancer. It is also known that EGF type tyrosine kinase activity is rarely detected in normal cells whereas it is more frequently detectable in malignant cells (Hunter, *Cell,* 1987, 50, 823). It has been shown more recently (W J Gullick, *Brit. Med. Bull.,* 1991, 47, 87) that EGF receptors which possess tyrosine kinase activity are overexpressed in many human cancers such as brain, lung squamous cell, bladder, gastric, breast, head and neck, oesophageal, gynaecological and thyroid tumours.

Accordingly it has been recognised that an inhibitor of receptor tyrosine kinases should be of value as a selective inhibitor of the growth of mammalian cancer cells (Yaish et al. *Science,* 1988, 242, 933). Support for this view is provided by the demonstration that erbstatin, an EGF receptor tyrosine kinase inhibitor, specifically attenuates the growth in athymic nude mice of a transplanted human mammary carcinoma which expresses EGF receptor tyrosine kinase but is without effect on the growth of another carcinoma which does not express EGF receptor tyrosine kinase (Toi et al., *Eur. J. Cancer Clin. Oncol.,* 1990, 26, 722.) Various derivatives of styrene are also stated to possess tyrosine kinase inhibitory properties (European Patent Application Nos. 0211363, 0304493 and 0322738) and to be of use as anti-tumour agents. The in vivo inhibitory effect of two such styrene derivatives which are EGF receptor tyrosine kinase inhibitors has been demonstrated against the growth of human squamous cell carcinoma inoculated into nude mice (Yoneda et al., *Cancer Research,* 1991, 51, 4430). Various known tyrosine kinase inhibitors are disclosed in a more recent review by T R Burke Jr. (*Drugs of the Future,* 1992, 17, 119).

It is known from European Patent Applications Nos. 0520722, 0566226 and 0635498 that certain quinazoline derivatives which bear an anilino substituent at the 4-position possess receptor tyrosine kinase inhibitory activity. It is further known from European Patent Application No. 0602851 that certain quinazoline derivatives which bear a heteroarylamino substituent at the 4-position also possess receptor tyrosine kinase inhibitory activity.

It is further known from International Patent Application WO 92/20642 that certain aryl and heteroaryl compounds inhibit EGF and/or PDGF receptor tyrosine kinase. There is the disclosure of certain quinazoline derivatives therein but no mention is made of 4-anilinoquinazoline derivatives.

The in vitro anti-proliferative effect of a 4-anilinoquinazoline derivative has been disclosed by Fry et al., *Science,* 1994, 265, 1093. It was stated that the compound 4-(3'-bromoanilino)-6,7-dimethoxyquinazoline was a highly potent inhibitor of EGF receptor tyrosine kinase.

The in vivo inhibitory effect of a 4,5-dianilinophthalimide derivative which is an inhibitor of the EGF family of receptor tyrosine kinases has been demonstrated against the growth in BALB/c nude mice of a human epidermoid carcinoma A-431 or of a human ovarian carcinoma SKOV-3 (Buchdunger et al., *Proc. Nat. Acad. Sci.,* 1994, 91, 2334).

It is further known from European Patent Application No. 0635507 that certain tricyclic compounds which comprise a 5- or 6-membered ring fused to the benzo-ring of a quinazoline possess receptor tyrosine kinase inhibitory activity. It is also known from European Patent Application No. 0635498 that certain quinazoline derivatives which carry an amino group at the 6-position and a halogeno group at the 7-position possess receptor tyrosine kinase inhibitory activity.

Accordingly it has been indicated that Class I receptor tyrosine kinase inhibitors will prove to be useful in the treatment of a variety of human cancers.

It is also expected that inhibitors of EGF type receptor tyrosine kinases will be useful in the treatment of other diseases of excessive cellular proliferation such as psoriasis (where TGFα is believed to be the most important growth factor) and benign prostatic hypertrophy (BPH).

There is no disclosure in these documents of quinazoline derivatives which bear at the 4-position a halogeno-substituted anilino substituent and which also bear a dialkylaminoalkoxy substituent at the 6-position. We have now found that such compounds possess potent in vivo anti-proliferative properties which are believed to arise from their Class I receptor tyrosine kinase inhibitory activity.

According to the present invention there is provided a quinazoline derivative of the formula I

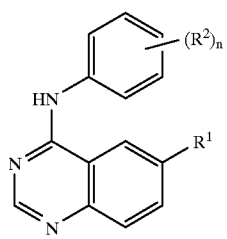

I wherein
n is 1, 2 or 3 and each $R^2$ is independently halogeno; and
$R^1$ is di-[(1–4C)alkyl]amino-(2–4C)alkoxy, pyrrolidin-1-yl-(2–4C)alkoxy, piperidino-(2–4C)alkoxy, morpholino-(2–4C)alkoxy, piperazin-1-yl-(2–4C)alkoxy or 4-(1–4C)alkylpiperazin-1-yl-(2–4C)alkoxy;
or a pharmaceutically-acceptable salt thereof.

In this specification the term "alkyl" includes both straight and branched chain alkyl groups but references to individual alkyl groups such as "propyl" are specific for the straight chain version only. For example when $R^1$ is a di-[(1–4C)alkyl]amino-(2–4C)alkoxy group, suitable values for this generic radical include 2-dimethylaminoethoxy, 3-dimethylaminopropoxy, 2-dimethylaminopropoxy and 1-dimethylaminoprop-2-yloxy. An analogous convention applies to other generic terms.

Within the present invention it is to be understood that, insofar as certain of the compounds of the formula I may exist in optically active or racemic forms by virtue of one or more substituents containing an asymmetric carbon atom, the invention encompasses any such optically active or racemic form which possesses anti-proliferative activity. The synthesis of optically active forms may be carried out by standard techniques of organic chemistry well known in the art, for example by synthesis from optically active starting materials or by resolution of a racemic form.

The quinazolines of the formula I are unsubstituted at the 2-, 5- and 8-positions.

It is also to be understood that certain quinazoline derivatives of the formula I can exist in solvated as well as unsolvated forms such as, for example, hydrated forms. It is to be understood that the invention encompasses all such solvated forms which possess anti-proliferative activity.

Suitable values for the generic radicals referred to above include those set out below.

A suitable value for $R^2$ when it is halogeno is, for example fluoro, chloro, bromo or iodo.

Suitable values for each $R^1$ substituent which may be present on the quinazoline ring include, for example:

| | |
|---|---|
| for di-[(1-4C)alkyl]amino-(2-4C)alkoxy: | 2-dimethylaminoethoxy, 2-(N-ethyl-N-methylamino)ethoxy, 2-diethylaminoethoxy, 2-dipropylaminoethoxy, 3-dimethylaminopropoxy, 3-diethylaminopropoxy, 2-dimethylaminopropoxy, 2-diethylaminopropoxy, 1-dimethylaminoprop-2-yloxy, 1-diethylaminoprop-2-yloxy, 1-dimethylamino-2-methylprop-2-yloxy, 2-dimethylamino-2-methylpropoxy, 4-dimethylaminobutoxy, 4-diethylaminobutoxy, 3-dimethylaminobutoxy, 3-diethylaminobutoxy, 2-dimethylaminobutoxy, 2-diethylaminobutoxy, 1-dimethylaminobut-2-yloxy and 1-diethylaminobut-2-yloxy; |
| for pyrrolidin-1-yl-(2-4C)-alkoxy: | 2-(pyrrolidin-1-yl)ethoxy, 3-(pyrrolidin-1-yl)propoxy and 4-(pyrrolidin-1-yl)butoxy; |
| for piperidino-(2-4C)alkoxy: | 2-piperidinoethoxy, 3-piperidinopropoxy and 4-piperidinobutoxy; |
| for morpholino-(2-4C)alkoxy: | 2-morpholinoethoxy, 3-morpholinopropoxy and 4-morpholinobutoxy; |
| for piperazin-1-yl-(2-4C)alkoxy: | 2-(piperazin-1-yl)ethoxy, 3-(piperazin-1-yl)propoxy and 4-(piperazin-1-yl)butoxy; |
| for 4-(1-4C)alkylpiperazin-1-yl-(2-4C)alkoxy: | 2-(4-methylpiperazin-1-yl)ethoxy, 3-(4-methylpiperazin-1-yl)propoxy and 4-(4-methylpiperazin-1-yl)butoxy. |

A suitable pharmaceutically-acceptable salt of a quinazoline derivative of the invention is, for example, a mono- or di-acid-addition salt of a quinazoline derivative of the invention which is sufficiently basic, for example, an acid-addition salt with, for example, an inorganic or organic acid, for example hydrochloric, hydrobromic, sulphuric, phosphoric, trifluoroacetic, citric, maleic, tartaric, fumaric, methanesulphonic or 4-toluenesulphonic acid.

Particular novel compounds of the invention include, for example, quinazoline derivatives of the formula I, or pharmaceutically-acceptable salts thereof, wherein:

(a) n is 1 or 2 and each $R^2$ is independently fluoro, chloro or bromo; and $R^1$ has any of the meanings defined hereinbefore or in this section relating to particular novel compounds of the invention;

(b) $R^1$ is 2-dimethylaminoethoxy, 2-diethylaminoethoxy, 3-dimethylaminopropoxy, 3-diethylaminopropoxy, 2-(pyrrolidin-1-yl)ethoxy, 3-(pyrrolidin-1-yl)propoxy, 2-piperidinoethoxy, 3-piperidinopropoxy, 2-morpholinoethoxy, 3-morpholinopropoxy, 2-(piperazin-1-yl)ethoxy, 3-(piperazin-1-yl)propoxy, 2-(4-methylpiperazin-1-yl)ethoxy or 3-(4-methylpiperazin-1-yl)propoxy;
and n and $R^2$ have any of the meanings defined hereinbefore or in this section relating to particular novel compounds of the invention.

A preferred compound of the invention is a quinazoline derivative of the formula I wherein $(R^2)_n$ is 3'-chloro, 3'-bromo, 2',4'-difluoro, 2',4'-dichloro, 3',4'-difluoro, 3',4'-dichloro, 3'-fluoro-4'-chloro or 3'-chloro-4'-fluoro;

and $R^1$ is 2-dimethylaminoethoxy, 2-diethylaminoethoxy, 3-dimethylaminopropoxy, 3-diethylaminopropoxy, 2-(pyrrolidin-1-yl)ethoxy, 3-(pyrrolidin-1-yl)propoxy, 2-piperidinoethoxy, 3-piperidinopropoxy, 2-morpholinoethoxy or 3-morpholinopropoxy;

or a pharmaceutically-acceptable acid-addition salt thereof.

A further preferred compound of the invention is a quinazoline derivative of the forula I wherein $(R^2)_n$ is 3',4'-difluoro or 3'-chloro-4'-fluoro;

and $R^1$ is 3-dimethylaminopropoxy, 3-diethylaminopropoxy, 3-(pyrrolidin-1-yl)propoxy, 3-piperidinopropoxy or 3-morpholinopropoxy;

or a pharmaceutically-acceptable acid-addition salt thereof.

According to a further aspect of the present invention there is provided the quinazoline derivative 4-(3'-chloro-4'-fluoroanilino)-6-(3-diethylaminopropoxy)quinazoline;

or a pharmaceutically-acceptable salt thereof.

According to a further aspect of the present invention there is provided the quinazoline derivative 4-(3',4'-difluoroanilino)-6-(3-morpholinopropoxy)quinazoline;

or a pharmaceutically-acceptable salt thereof.

It is also to be understood that these quinazoline derivatives of the invention can exist in solvated as well as unsolvated forms such as, for example, hydrated forms. It is to be understood that the invention encompasses all such solvated forms which possess anti-proliferative activity.

The quinazoline derivatives of the invention, or pharmaceutically-acceptable salts thereof, may be prepared by any process known to be applicable to the preparation of chemically-related compounds. Suitable processes include, for example, those illustrated in European Patent Applications Nos. 0520722, 0566226, 0602851, 0635498 and 0635507. Such processes, when used to prepare the quinazoline derivatives of the invention, or pharmaceutically-acceptable salts thereof, are provided as a further feature of the invention and are illustrated by the following representative Examples. Necessary starting materials may be obtained by standard procedures of organic chemistry. The preparation of such starting materials is described within the accompanying non-limiting Examples. Alternatively necessary starting materials are obtainable by analogous procedures to those illustrated which are within the ordinary skill of an organic chemist.

(a) The reaction, conveniently in the presence of a suitable base, of a quinazoline of the formula II

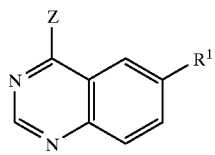

II wherein Z is a displaceable group, with an aniline of the formula III

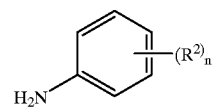

III

A suitable displaceable group Z is, for example, a halogeno, alkoxy, aryloxy or sulphonyloxy group, for example a chloro, bromo, methoxy, phenoxy, methanesulphonyloxy or toluene-4-sulphonyloxy group.

A suitable base is, for example, an organic amine base such as, for example, pyridine, 2,6-lutidine, collidine, 4-dimethylaminopyridine, triethylamine, morpholine, N-methylmorpholine or diazabicyclo[5.4.0]undec-7-ene, or, for example, an alkali or alkaline earth metal carbonate or hydroxide, for example sodium carbonate, potassium carbonate, calcium carbonate, sodium hydroxide or potassium hydroxide. Alternatively a suitable base is, for example, an alkali metal or alkaline earth metal amide, for example sodium amide or sodium bis(trimethylsilyl)amide.

The reaction is preferably carried out in the presence of a suitable inert solvent or diluent, for example an alkanol or ester such as methanol, ethanol, isopropanol or ethyl acetate, a halogenated solvent such as methylene chloride, chloroform or carbon tetrachloride, an ether such as tetrahydrofuran or 1,4-dioxan, an aromatic solvent such as toluene, or a dipolar aprotic solvent such as N,N-dimethylformamide, N,N-dimethylacetamide, N-methylpyrrolidin-2-one or dimethylsulphoxide. The reaction is conveniently carried out at a temperature in the range, for example, 10 to 150° C., preferably in the range 20 to 80° C.

The quinazoline derivatives of the invention may be obtained from this process in the form of the free base or alternatively they may be obtained in the form of a salt with the acid of the formula H-Z wherein Z has the meaning defined hereinbefore. When it is desired to obtain the free base from the salt, the salt may be treated with a suitable base as defined hereinbefore using a conventional procedure.

(b) For the production of the compounds of the formula I wherein $R^1$ is an amino-substituted (2–4C)alkoxy group, the alkylation, conveniently in the presence of a suitable base as defined hereinbefore, of a quinazoline derivative of the formula I wherein $R^1$ is a hydroxy group.

The reaction is preferably carried out in a suitable inert solvent or diluent as defined hereinbefore and at a temperature in the range, for example, 0 to 150° C., conveniently at or near 90° C.

(c) For the production of those compounds of the formula I wherein $R^1$ is an amino-substituted (2–4C)alkoxy group, the reaction, conveniently in the presence of a suitable base as defined hereinbefore, of a compound of the formula I wherein $R^1$ is a hydroxy-(2–4 C) alkoxy group, or a reactive derivative thereof, with an appropriate amine.

A suitable reactive derivative of a compound of the formula I wherein $R^1$ is a hydroxy-(2–4C)alkoxy group is, for example, a halogeno- or sulphonyloxy-(2–4C)alkoxy group such as a bromo- or methanesulphonyloxy-(2–4C) alkoxy group.

The reaction is preferably carried out in the presence of a suitable inert solvent or diluent as defined hereinbefore and at a temperature in the range, for example, 10 to 150° C., conveniently at or near 50° C.

When a pharmaceutically-acceptable salt of a quinazoline derivative of the invention is required, for example a mono- or di-acid-addition salt of the quinazoline derivative of the invention, it may be obtained, for example, by reaction of said compound with, for example, a suitable acid using a conventional procedure.

As stated hereinbefore the quinazoline derivatives defined in the present invention possess anti-proliferative activity which is believed to arise from the Class I receptor tyrosine-kinase inhibitory activity of the compounds. These properties may be assessed, for example, using one or more of the procedures set out below:

(a) An in vitro assay which determines the ability of a test compound to inhibit the enzyme EGF receptor tyrosine kinase. Receptor tyrosine kinase was obtained in partially purified form from A-431 cells (derived from human vulval carcinoma) by the procedures described below which are related to those described by Carpenter et al., *J. Biol. Chem.,* 1979, 254, 4884, Cohen et al., *J. Biol. Chem.,* 1982, 257, 1523 and by Braun et al., *J. Biol. Chem.,* 1984, 259, 2051.

A-431 cells were grown to confluence using Dulbecco's modified Eagle's medium (DMEM) containing 5% fetal calf serum (FCS). The obtained cells were homogenised in a hypotonic borate/EDTA buffer at pH 10.1. The homogenate was centrifuged at 400 g for 10 minutes at 0–4° C. The supernatant was centrifuged at 25,000 g for 30 minutes at 0–4° C. The pelleted material was suspended in 30 mM Hepes buffer at pH 7.4 containing 5% glycerol, 4 mM benzamidine and 1% Triton X-100, stirred for 1 hour at 0–4° C., and recentrifuged at 100,000 g for 1 hour at 0–4° C. The supernatant, containing solubilised receptor tyrosine kinase, was stored in liquid nitrogen.

For test purposes 40 µl of the enzyme solution so obtained was added to a mixture of 400 µl of a mixture of 150 mM Hepes buffer at pH 7.4. 500 µM sodium orthovanadate, 0.1% Triton X-100, 10% glycerol, 200 µl water, 80 µl of 25 mM DTT and 80 µl of a mixture of 12.5 mM manganese chloride, 125 mM magnesium chloride and distilled water. There was thus obtained the test enzyme solution.

Each test compound was dissolved in dimethylsulphoxide (DMSO) to give a 50 mM solution which was diluted with 40 mM Hepes buffer containing 0.1% Triton X-100, 10% glycerol and 10% DMSO to give a 500 µM solution. Equal volumes of this solution and a solution of epidermal growth factor (EGF; 20 µg/ml) were mixed.

[γ-$^{32}$P]ATP (3000 Ci/mM, 250 µCi) was diluted to a volume of 2 ml by the addition of a solution of ATP (100 µM) in distilled water. An equal volume of a 4 mg/ml solution of the peptide Arg-Arg-Leu-Ile-Glu-Asp-Ala-Glu-Tyr-Ala-Ala-Arg-Gly in a mixture of 40 mM Hepes buffer at pH 7.4, 0.1% Triton X-100 and 10% glycerol was added.

The test compound/EGF mixture solution (5 µl) was added to the test enzyme solution (10 µl) and the mixture was incubated at 0–4° C. for 30 minutes. The ATP/peptide mixture (10 µl) was added and the mixture was incubated at 25° C. for 10 minutes. The phosphorylation reaction was terminated by the addition of 5% trichloroacetic acid (40 µl) and bovine serum albumin (BSA; 1 mg/ml, 5 µl). The mixture was allowed to stand at 4° C. for 30 minutes and then centrifuged. An aliquot (40 µl) of the supernatant was placed onto a strip of Whatman p 81 phosphocellulose paper. The strip was washed in 75 mM phosphoric acid (4×10 ml) and blotted dry. Radioactivity present in the filter paper was measured using a liquid scintillation counter (Sequence A). The reaction sequence was repeated in the absence of the EGF (Sequence B) and again in the absence of the test compound (Sequence C).

Receptor tyrosine kinase inhibition was calculated as follows:

$$\% \text{ Inhibition} = \frac{100 - (A - B)}{C - B} \times 100$$

The extent of inhibition was then determined at a range of concentrations of test compound to give an IC$_{50}$ value.

(b) An in vitro assay which determines the ability of a test compound to inhibit the EGF-stimulated growth of the human naso-pharyngeal cancer cell line KB.

KB cells were seeded into wells at a density of 1×10$^4$–1.5×10$^4$ cells per well and grown for 24 hours in DMEM supplemented with 5% FCS (charcoal-stripped). Cell growth was determined after incubation for 3 days by the extent of metabolism of MTT tetrazolium dye to furnish a bluish colour. Cell growth was then determined in the presence of EGF (10 ng/ml) or in the presence of EGF (10 ng/ml) and a test compound at a range of concentrations. An IC$_{50}$ value could then be calculated.

(c) An in-vivo assay in a group of athymic nude mice (strain ONU:Alpk) which determines the ability of a test compound (usually administered orally as a ball-milled suspension in 0.5% polysorbate) to inhibit the growth of xenografts of the human vulval epidermoid carcinoma cell line A-431.

A-431 cells were maintained in culture in DMEM supplemented with 5% FCS and 2 mM glutamine. Freshly cultured cells were harvested by trypsinization and injected subcutaneously (10 million cells/0.1 ml/mouse) into both flanks of a number of donor nude mice. When sufficient tumour material was available (after approximately 9 to 14 days), fragments of tumour tissue were transplanted in the flanks of recipient nude mice (test day 0). Generally, on the seventh day after transplantation (test day 7) groups of 7 to 10 mice with similar-sized tumours were selected and dosing of the test compound was commenced. Once daily dosing of test compound was continued for a total of 13 days (test days 7 to 19 inclusive). In some studies the dosing of the test compound was continued beyond test day 19, for example to test day 26. In each case, on the following test day the animals were killed and the final tumour volume was calculated from measurements of the length and width of the tumours. Results were calculated as a percentage inhibition of tumour volume relative to untreated controls.

The compounds of the inventions in general, possess activity at approximately the following concentrations or doses in tests (a) to (c):

Test (a):- IC$_{50}$ in the range, for example, 0.001 to 1 µM;
Test (b):- IC$_{50}$ in the range, for example, 0.1 to 1 µM;
Test (c):- 20 to 90% inhibition of tumour volume from a daily dose in the range, for example, 12.5 to 200 mg/kg.

The quinazoline derivative 4-(3'-chloro-4'-fluoroanilino)-6-(3-diethylaminopropoxy)quinazoline possesses activity at approximately the following concentrations or doses:—Test (a): IC$_{50}$ 0.003 µM; Test (b): IC$_{50}$0.1 µM; Test (c): greater than 50% inhibition of tumour volume from a daily dose of 50 mg/kg.

The quinazoline derivative 4-(3',4'-difluoroanilino)-6-(3-morpholinopropoxy)quinazoline possesses activity at approximately the following concentrations or doses: Test (b): IC$_{50}$ 1.2 µM; Test (c): greater than 50% inhibition of tumour volume from a daily dose of 50 mg/kg.

According to a further aspect of the invention there is provided a pharmaceutical composition which comprises a quinazoline derivative of the formula I, or a pharmaceutically-acceptable salt thereof, in association with a pharmaceutically-acceptable diluent or carrier.

The composition may be in a form suitable for oral administration, for example as a tablet or capsule, for parenteral injection (including intraveous, subcutaneous, intramuscular, intravascular or infusion) as a sterile solution, suspension or emulsion, for topical administration as an ointment or cream or for rectal administration as a suppository.

In general the above compositions may be prepared in a conventional manner using conventional excipients.

The quinazoline derivative will normally be administered to a warm-blooded animal at a unit dose within the range 5–10000 mg per square meter body area of the animal, i.e. approximately 0.1–200 mg/kg, and this normally provides a therapeutically-effective dose. A unit dose form such as a tablet or capsule will usually contain, for example 1–250 mg of active ingredient. Preferably a daily dose in the range of 1–100 mg/kg is employed. However the daily dose will necessarily be varied depending upon the host treated, the particular route of administration, and the severity of the illness being treated. Accordingly the optimum dosage may be determined by the practitioner who is treating any particular patient.

According to a further aspect of the present invention there is provided a quinazoline derivative of the formula I, or a pharmaceutically-acceptable salt thereof, for use in a method of treatment of the human or animal body by therapy.

We have now found that the compounds of the present invention possess anti-proliferative properties such as anti-cancer properties which are believed to arise from their Class I receptor tyrosine kinase inhibitory activity. Accordingly the compounds of the present invention are expected to be useful in the treatment of diseases or medical conditions mediated alone or in part by Class I receptor tyrosine kinases, i.e. the compounds may be used to produce a Class I receptor tyrosine kinase inhibitory effect in a warm-blooded animal in need of such treatment. Thus the compounds of the present invention provide a method for treating the proliferation of malignant cells characterised by inhibition of Class I receptor tyrosine kinases, i.e. the compounds may be used to produce an anti-proliferative effect mediated alone or in part by the inhibition of Class I receptor tyrosine kinase. Accordingly the compounds of the present invention are expected to be useful in the treatment of psoriasis and/or cancer by providing an anti-proliferative effect, particularly in the treatment of Class I receptor tyrosine kinase sensitive cancers such as cancers of the breast, lung, colon, rectum, stomach, prostate, bladder, pancreas and ovary.

Thus according to this aspect of the invention there is provided the use of a quinazoline derivative of the formula I, or a pharmaceutically-acceptable salt thereof, in the manufacture of a medicament for use in the production of an anti-proliferative effect in a warm-blooded animal such as man.

According to a further feature of this aspect of the invention there is provided a method for producing an anti-proliferative effect in a warm-blooded animal, such as man, in need of such treatment which comprises administering to said animal an effective amount of a quinazoline derivative as defined immediately above.

As stated above the size of the dose required for the therapeutic or prophylactic treatment of a particular proliferative disease will necessarily be varied depending on the host treated, the route of administration and the severity of the illness being treated. A unit dose in the range, for example, 1–200 mg/kg, preferably 1–100 mg/kg is envisaged.

The anti-proliferative treatment defined hereinbefore may be applied as a sole therapy or may involve, in addition to the quinazoline derivative of the invention, one or more other anti-tumour substances, for example those selected from, for example, mitotic inhibitors, for example vinblastine, vindesine and vinorelbine; tubulin disassembly inhibitors such as taxol; alkylating agents, for example cis-platin, carboplatin and cyclophosphamide; antimetabolites, for example 5-fluorouracil, tegafur, methotrexate, cytosine arabinoside and hydroxyurea, or, for example, one of the preferred antimetabolites disclosed in European Patent Application No. 239362 such as N-{5-[N-(3,4-dihydro-2-methyl-4-oxoquinazolin-6-ylmethyl)-N-methylamino]-2-thenoyl}-L-glutamic acid; intercalating antibiotics, for example adriamycin, mitomycin and bleomycin; enzymes, for example asparaginase; topoisomerase inhibitors, for example etoposide and camptothecin; biological response modifiers, for example interferon; and anti-hormones, for example antioestrogens such as tamoxifen or, for example antiandrogens such as 4'-cyano-3-(4-fluorophenylsulphonyl)-2-hydroxy-2-methyl-3'-(trifluoromethyl)propionanilide. Such conjoint treatment may be achieved by way of the simultaneous, sequential or separate dosing of the individual components of the treatment. According to this aspect of the invention there is provided a pharmaceutical product comprising a quinazoline derivative of the formula I as defined hereinbefore and an additional anti-tumour substance as defined hereinbefore for the conjoint treatment of cancer.

As stated above the quinazoline derivative defined in the present invention is an effective anti-cancer agent, which property is believed to arise from its Class I receptor tyrosine kinase inhibitory properties. Such a quinazoline derivative of the invention is expected to possess a wide range of anti-cancer properties as Class I receptor tyrosine kinases have been implicated in many common human cancers such as leukaemia and breast, lung, colon, rectal, stomach, prostate, bladder, pancreas and ovarian cancer. Thus it is expected that the quinazoline derivative of the invention will possess anti-cancer activity against these cancers. It is in addition expected that the quinazoline derivative of the present invention will possess activity against a range of leukaemias, lymphoid malignancies and solid tumours such as carcinomas and sarcomas in tissues such as the liver, kidney, prostate and pancreas.

It is further expected that a quinazoline derivative of the invention will possess activity against other diseases involving excessive cellular proliferation such as psoriasis, benign prostatic hypertrophy (BPH) and atherosclerosis.

It is also to be expected that a quinazoline derivative of the invention will be useful in the treatment of additional disorders of cellular growth in which aberrant cell signalling by way of receptor tyrosine kinase enzymes, including as yet unidentified receptor tyrosine kinase enzymes, are involved. Such disorders include, for example, inflammation, angiogenesis, vascular restenosis, immunological disorders, pancreatitis, kidney disease and blastocyte maturation and implantation.

The invention will now be illustrated in the following non-limiting Examples in which, unless otherwise stated:

(i) evaporations were carried out by rotary evaporation in vacuo and work-up procedures were carried out after removal of residual solids such as drying agents by filtration, unless otherwise stated magnesium sulphate was used as a drying agent for organic solutions:

(ii) operations were carried out at ambient temperature, that is in the range 18–25° C. and under an atmosphere of an inert gas such as argon;

(iii) column chromatography (by the flash procedure) and medium pressure liquid chromatography (MPLC) were performed on Merck Kieselgel silica (Art. 9385) or Merck Lichroprep RP-18 (Art. 9303) reversed-phase silica obtained from E. Merck, Darmstadt, Germany;

(iv) yields are given for illustration only and are not necessarily the maximum attainable;

(v) melting points were determined using a Mettler SP62 automatic melting point apparatus, an oil-bath apparatus or a Koffler hot plate apparatus.

(vi) the structure of the compound of the invention was confirmed by nuclear (generally proton) magnetic resonance (NMR) and mass spectral techniques; proton magnetic resonance chemical shift values were measured on the delta scale and peak multiplicities are shown as follows: s, singlet; d, doublet; t, triplet; m, multiplet, unless otherwise stated end-products of the invention were dissolved in $CD_3SOCD_3$ for the determination of NMR values;

(vii) intermediates were not generally fully characterised and purity was assessed by thin layer chromatography (TLC), infra-red (IR) or NMR analysis;

(viii) the following abbreviation has been used:

DMA N,N-dimethylacetamide;
DMF N,N-dimethylformamide.

EXAMPLE 1

A mixture of 4-(3'-chloro-4'-fluoroanilino)-6-hydroxyquinazoline (2 g), 3-diethylaminopropyl chloride hydrochloride (1.42 g), potassium carbonate (5 g) and DMA (75 ml) was stirred and heated to 90° C. for 3 hours. The mixture was cooled to ambient temperature and filtered. The filtrate was evaporated and the residue was purified by column chromatography using increasingly polar mixtures of methylene chloride and methanol as eluent. The material so obtained was triturated under diethyl ether. There was thus obtained 4-(3'-chloro-4'-fluoroanilino)-6-(3-diethylaminopropoxy)quinazoline (1.06 g, 38%), m.p. 138–140° C.; NMR Spectrum: 1.0 (t, 6H), 1.98 (m, 2H), 2.65 (m, 6H), 4.21 (t, 2H), 7.45 (t, 1H),7.53 (m, 1H), 7.76 (d, 1H), 7.88 (m, 1H), 7.92 (d,1H), 8.18 (m, 1H), 8.53 (s, 1H), 9.73 (broad s, 1H); Elemental Analysis: Found C, 61.2; H, 5.8; N, 13.9; $C_{21}H_{24}ClFN_4O$ $0.5H_2O$ requires C, 61.2; H, 6.1; N, 13.6%.

The 4-(3'-chloro-4'-fluoroanilino)-6-hydroxyquinazoline used as a starting material was obtained as follows:

A mixture of 6-acetoxy-4-chloroquinazoline (European Patent Application No. 0566226, Example 34, Note c; 54 g), 3-chloro-4-fluoroaniline (35.6 g) and isopropanol (850 ml) was stirred and heated to reflux for 90 minutes and then stored at ambient temperature for 16 hours. The precipitate was isolated and washed in turn with isopropanol and ether. There was thus obtained 6-acetoxy-4-(3'-chloro-4'-fluoroanilino)quinazoline (43.7 g, 49%).

A concentrated aqueous ammonium hydroxide solution (30% weight/volume, 35 ml) was added to a stirred mixture of 6-acetoxy-4-(3'-chloro-4'-fluoroanilino)quinazoline (22 g) and methanol (200 ml) and the mixture was heated to reflux for 3 hours. The mixture was evaporated and water (300 ml) was added to the residue. The solid was isolated, washed in turn with water (100 ml) and ethanol (60 ml) and dried. There was thus obtained 4-(3'-chloro-4'-fluoroanilino)-6-hydroxyquinazoline (16.1 g, 93%). NMR Spectrum: 7.43 (t, 1H), 7.45 (m, 1H), 7.70 (d, 1H), 7.78 (d. 1H), 7.88 (m, 1H), 8.24 (m, 1H), 8.5 (s, 1H), 9.6 (broad s, 1H), 10.1 (broad s, 1H).

EXAMPLE 2

A mixture of 4-(3',4'-difluoroanilino)-6-hydroxyquinazoline (1.53 g), 3-morpholinopropyl chloride (*J. Amer. Chem. Soc.*, 1945, 67, 736; 1.5 g), potassium carbonate (4 g) and DMF (150 ml) was stirred and heated to 105° C. for 4 hours. The mixture was cooled to ambient temperature and filtered. The filtrate was evaporated and the residue was purified by column chromatography using increasingly polar mixtures of methylene chloride and methanol as eluent. There was thus obtained 4-(3',4'-difluoroanilino)-6-(3-morpholinopropoxy)quinazoline (1.22 g, 54%), m.p. 181–183° C.; NMR Spectrum: 2.0 (m, 2H), 2.4 (m, 4H), 3.6 (t, 4H), 4.2 (t, 2H), 7.4–7.55 (m, 2H), 7.6 (m, 1H), 7.75 (d, 1H), 7.9 (d, 1H), 8.1 (m, 1H), 8.5 (s, 1H), 9.7 (broad s, 1H); Elemental Analysis: Found C, 63.3; H, 5.7; N, 13.9; $C_{21}H_{22}F_2N_4O_2$ requires C, 63.0; H, 5.5; N, 14.0%.

The 4-(3',4'-difluoroanilino)-6-hydroxyquinazoline used as a starting material was obtained as follows:

A mixture of 6-acetoxychloroquinazoline (16.5 g), 3',4'-difluoroaniline (10.4 g) and isopropranol (400 ml) was stirred and heated to reflux for 2 hours. The mixture was cooled to ambient temperature. The precipitate was isolated and triturated under a mixture of methylene chloride, methanol and triethylamine. The resultant solid was isolated and dried. There was thus obtained 6-acetoxy-4-(3',4'-difluoroanilino)quinazoline (14 g), m.p.>250° C.

A mixture of the material so obtained, a concentrated (30% weight/volume, 25 ml) aqueous ammonium hydroxide solution and methanol (300 ml) was stirred and heated to reflux for 3 hours. The mixture was evaporated. The residue was suspended in water (400 ml) and stirred for 15 minutes. The mixture was filtered and the solid was washed in turn with water and with diethyl ether and then dried. There was thus obtained 4-(3',4'-difluoroanilino)-6-hydroxyquinazoline (9.8 g), m.p.>250° C.; NMR Spectrum: 7.45 (m, 2H), 7.7 (m, 2H), 8.0 (d, 1H), 8.15 (m, 1H), 8.5 (s, 1H), 9.6 (broad s, 1H), 10.1 (broad s, 1H); Elemental Analysis: Found C, 60.7; H, 3.3; N, 15.3; $C_{14}H_9F_2N_3O$ $0.1H_2O$ requires C, 61.1; H, 3.4; N, 15.3%.

EXAMPLE 3

Using an analogous procedure to that described in Example 1, 4-(3'-chloro-4'-fluoroanilino)-6-hydroxyquinazoline was reacted with 3-dimethylaminopropyl chloride hydrochloride to give 4-(3'-chloro-4'-fluoroanilino)-6-(3-dimethylaminopropoxy)quinazoline in 72% yield; NMR Spectrum: 1.98 (m, 2H), 2.34 (s, 6H), 2.51 (t, 2H), 4.22 (t, 2H), 7.48 (t, 1H), 7.52 (m, 1H), 7.75 (d, 1H), 7.85 (m, 1H), 7.91 (m, 1H), 8.18 (m, 1H), 8.54 (s, 1H), 9.72 (broad s, 1H); Elemental Analysis: Found C, 60.5; H, 5.3; N, 14.9; $C_{19}H_{20}ClFN_4O$ requires C, 60.5l; H, 5.3; N, 14.9%.

EXAMPLE 4

Using an analogous procedure to that described in Example 1,4-(3'-chloro-4'-fluoroanilino)-6-hydroxquinazoline was reacted with 3-piperidinopropyl chloride hydrochloride to give 4-(3'-chloro-4'-fluoroanilino)-6-(3-piperidinopropoxy)quinazoline in 40% yield; NMR Spectrum: 1.43 (m, 2H), 1.53 (m, 4H), 2.01 (m, 2H), 2.45 (m, 6H), 4.2 (t, 2H), 7,44 (t, 1H), 7.5 (m, 1H), 7.74 (d, 1H), 7.84 (m, 1H), 7.92 (d, 1H), 8.17 (m, 1H), 8.53 (s, 1H), 10.7 (broad s, 1H); Elemental Analysis: Found C, 60.4;

H, 5.1; N, 12.8; $C_{22}H_{24}ClFN_4O$ $0.1H_2O$ $0.2K_2CO_3$ requires C, 60.0; H, 5.5; N, 12.6%.

EXAMPLE 5

Using an analogous procedure to that described in Example 1 except that the reaction mixture was heated to 100° C. for 16 hours, 4-(3'-chloro-4'-fluoroanilino)-6-hydroxyquinazoline was reacted with 3-(pyrrolidin-1-yl) propyl chloride hydrochloride (*Chem. Abs.*, 82, 57736) to give 4-(3'-chloro-4'-fluoroanilino)-6-(3-pyrrolidin-1-ylpropoxy)quinazoline in 45% yield; NMR Spectrum: 1.73 (m, 4H), 2.03 (m, 2H), 2.58 (m, 4H), 2.69 (t, 2H), 4.22 (t, 2H), 7.44 (t, 1H), 7.51 (m, 1H), 7.73 (d, 1H), 7.85 (m, 1H), 7.9 (d, 1H), 8.17 (m, 1H), 8.52 (s, 1H), 9.72 (broad s, 1H); Elemental Analysis: Found C, 62.3; H, 5.9; N. 13.7; $C_{21}H_{22}ClFN_4O$ $0.25H_2O$ requires C, 62.2; H, 5.6; N, 13.8%.

EXAMPLE 6

Using an analogous procedure to that described in Example 1 except that the reaction mixture was heated to 100° C. for 2 hours. 4-(3'-chloro-4'- fluoroanilino)-6-hydroxyquinazoline was reacted with 3-morpholinopropyl chloride to give 4-(3'-chloro-4'-fluoroanilino)-6-(3-morpholinopropoxy)quinazoline in 58% yield; NMR Spectrum: 1.97 (m, 2H), 2.4 (broad t, 4H), 2.48 (t, 2H), 3.58 (t, 4H), 4.2 (t, 2H), 7.44 (t, 1H), 7.53 (m, 1H) 7.74 (d, 1H), 7.85 (m, 1H), 7.9 (d, 1H), 8.17 (m, 1H), 8.53 (s, 1H), 9.67 (broad s, 1H); Elemental Analysis: Found C, 60.0; H, 5.4; N, 13.2; $C_{21}H_{22}ClFN_4O_2$ $0.2H_2O$ requires C, 60.0; H, 5.3; N, 13.3%.

EXAMPLE 7

The following illustrate representative pharmaceutical dosage forms containing the compound of formula I, or a pharmaceutically-acceptable salt thereof (hereafter compound X), for therapeutic or prophylactic use in humans:

| (a) Tablet I | mg/tablet |
|---|---|
| Compound X | 100 |
| Lactose Ph.Eur | 182.75 |
| Croscarmellose sodium | 12.0 |
| Maize starch paste (5% w/v paste) | 2.25 |
| Magnesium stearate | 3.0 |

| (b) Tablet II | mg/tablet |
|---|---|
| Compound X | 50 |
| Lactose Ph.Eur | 223.75 |
| Croscarmellose sodium | 6.0 |
| Maize starch | 15.0 |
| Polyvinylpyrrolidone | 2.25 |
| Magnesium stearate | 3.0 |

| (c) Tablet III | mg/tablet |
|---|---|
| Compound X | 1.0 |
| Lactose Ph.Eur | 93.25 |
| Croscarmellose sodium | 4.0 |
| Maize starch paste (5% w/v paste) | 0.75 |
| Magnesium stearate | 1.0 |

| (d) Capsule | mg/capsule |
|---|---|
| Compound X | 10 |
| Lactose Ph. Eur | 488.5 |
| Magnesium stearate | 1.5 |

| (e) Injection I | (50 mg/ml) |
|---|---|
| Compound X | 5.0% w/v |
| 1M Sodium hydroxide solution | 15.0% w/v |
| 0.1M Hydrochloric acid | |

| (to adjust pH to 7.6) | |
|---|---|
| Polyethylene glycol 400 | 4.5% w/v |
| Water for injection to 100% | |

| (f) Injection II | (10 mg/ml) |
|---|---|
| Compound X | 1.0% w/v |
| Sodium phosphate BP | 3.6% w/v |
| 0.1M Sodium hydroxide solution | 15.0% v/v |
| Water for injection to 100% | |

| (g) Injection III | (1 mg/ml,buffered to pH 6) |
|---|---|
| Compound X | 0.1% w/v |
| Sodium phosphate BP | 2.26% w/v |
| Citric acid | 0.38% w/v |
| Polyethylene glycol 400 | 3.5% w/v |
| Water for injection to 100% | |

Note
The above formulations may be obtained by conventional procedures well known in the pharmaceutical art. The tablets (a)–(c) may be enteric coated by conventional means, for example to provide a coating of cellulose acetate phthalate.

I claim:
1. A quinazoline derivative of the formula I

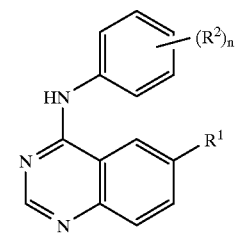

wherein
n is 1, 2 or 3 and each $R^2$ is independently halogeno;
and $R^1$ is di-[(1–4C)alkyl]amino-(2–4C)alkoxy. pyrrolidin-1-yl-(2–4C)alkoxy, piperidino-(2–4C) alkoxy, morpholino-(2–4C)alkoxy, piperazin-1-yl-(2–4C)alkoxy or 4-(1–4C)alkylpiperazin-1-yl-(2–4C) alkoxy;
or a pharmaceutically-acceptable salt thereof.
2. A quinazoline derivative of the formula I as claimed in claim 1 wherein $(R^2)_n$ is 3'-chloro, 3'-bromo, 2',4'-difluoro, 2',4'-dichloro, 3',4'-difluoro, 3',4'-dichloro, 3'-fluoro-4'-chloro or 3'-chloro-4'-fluoro;
and $R^1$ is 2-dimethylaminoethoxy, 2-diethylaminoethoxy, 3-dimethylaminopropoxy, 3-diethylaminopropoxy, 2-(pyrrolidin-1-yl)ethoxy, 3-(pyrrolidin-1-yl)propoxy, 2-piperidinoethoxy, 3-piperidinopropoxy, 2-morpholinoethoxy or 3-morpholinopropoxy;
or a pharmaceutically-acceptable acid-addition salt thereof.
3. A quinazoline derivative of the formula I as claimed in claim 1 wherein $(R^2)_n$ is 3',4'-difluoro or 3'-chloro-4'-fluoro;
and $R^1$ is 3-dimethylaminopropoxy, 3-diethylaminopropoxy, 3-(pyrrolidin-1-yl)propoxy, 3-piperidinopropoxy or 3-morpholinopropoxy;
or a pharmaceutically-acceptable acid-addition salt thereof.
4. The quinazoline derivative of the formula I as claimed in claim 1 being:
4-(3'-chloro-4'-fluoroanilino)-6-(3-diethylaminopropoxy) quinazoline;
or a pharmaceutically-acceptable salt thereof.
5. The quinazoline derivative of the formula I as claimed in claim 1 being:

4-(3',4'-difluoroanilino)-6-(3-morpholinopropoxy) quinazoline;
or a pharmaceutically-acceptable salt thereof.

6. A process for the preparation of a quinazoline derivative of the formula I, or a pharmaceutically-acceptable salt thereof, as claimed in any one of claims 1 to 5 which comprises:

(a) the reaction of a quinazoline of the formula II

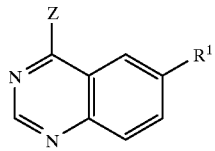

wherein Z is a displaceable group, with an aniline of the formula III

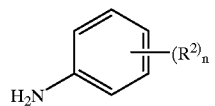

(b) for the production of the compounds of the formula I wherein $R^1$ is an amino-substituted (2–4C)alkoxy group, the alkylation of a quinazoline derivative of the formula I wherein $R^1$ is a hydroxy group;

(c) for the production of those compounds of the formula I wherein $R^1$ is an amino-substituted (2–4C)alkoxy group, the reaction of a compound of the formula I wherein $R^1$ is a hydroxy-(2–4C)alkoxy group, or a reactive derivative thereof, with an appropriate amine;

and when a pharmaceutically-acceptable salt of a quinazoline derivative of the invention is required it may be obtained by reaction of said compound with a suitable acid using a conventional procedure.

7. A pharmaceutical composition which comprises a quinazoline derivative of the formula I, or a pharmaceutically-acceptable salt thereof, as claimed in any one of claims 1 to 5 in association with a pharmaceutically-acceptable diluent or carrier.

8. A method for producing an anti-proliferative effect in a warm-blooded animal in need of such treatment which comprises administering to said animal an effective amount of a quinazoline derivative of the formula I, or a pharmaceutically-acceptable salt thereof, as claimed in any one of claims 1 to 5.

* * * * *